United States Patent [19]

Hedengren et al.

[11] Patent Number: 5,371,462
[45] Date of Patent: Dec. 6, 1994

[54] EDDY CURRENT INSPECTION METHOD EMPLOYING A PROBE ARRAY WITH TEST AND REFERENCE DATA ACQUISITION AND SIGNAL PROCESSING

[75] Inventors: Kristina H. V. Hedengren, Schenectady, N.Y.; Patrick J. Howard, Cincinnati, Ohio

[73] Assignee: General Electric Company, Schenectady, N.Y.

[21] Appl. No.: 34,916

[22] Filed: Mar. 19, 1993

[51] Int. Cl.$^5$ .................. G01N 27/90; G01R 33/12; G01R 17/00
[52] U.S. Cl. .................. 324/225; 324/219; 324/227; 324/232; 324/242; 364/571.01; 364/582
[58] Field of Search .............. 324/202, 219, 220, 225, 324/227, 232, 237, 238, 241, 242; 364/571.01, 582

[56] References Cited

U.S. PATENT DOCUMENTS

| | | | |
|---|---|---|---|
| 3,718,855 | 2/1973 | Rogel et al. | 324/202 |
| 4,194,149 | 3/1980 | Holt et al. | 324/220 |
| 4,578,643 | 3/1986 | Junker et al. | 324/202 |
| 4,763,274 | 8/1988 | Junker et al. | 324/220 X |
| 4,808,927 | 2/1989 | Cecco et al. | 324/220 |
| 5,124,641 | 6/1992 | Netter et al. | 324/219 X |
| 5,140,264 | 8/1992 | Metala et al. | 324/219 |

OTHER PUBLICATIONS

Probe-Flaw Interactions with Eddy Current Array Probes, by, Bert A. Auld, Review of Progress in Quantitative NDE 10, edited by D. O. Thompson et al. (Plenum Press, N.Y. 1991) pp. 951–955.

Electromagnetic Sensor Arrays—Experimental Studies, by A. J. Bahr, Review of Progress in Quantitative NDE 10, edited by D. O. Thompson et al. (Plenum Press, N.Y. 1991) pp. 691–698.

Flexible Substrate Eddy Current Coil Arrays, by Y. D. Krampfner et al., Review of Progress in Quantitative NDE 7, edited by D. O. Thompson et al. (Plenum Press, N.Y. 1988) pp. 471–478.

Advanced Eddy Current Array Defect Imaging, by M. Macecek, Review of Progress in Quantitative NDE 10, edited by D. O. Thompson et al. (Plenum Press, N.Y. 1991) pp. 995–1002.

Primary Examiner—Gerard R. Strecker
Attorney, Agent, or Firm—David C. Goldman; Paul R. Webb, II

[57] ABSTRACT

Disclosed are methods for processing and interpreting data acquired from an eddy current probe array inspection system, based on a background subtraction technique. Test and reference waveform data sets are acquired, and subsequently combined. However, the data sets are first normalized and registered to the same position, registering on characteristic signals produced when scanning over edges. Specific techniques are disclosed for normalizing, correcting for spatial offsets, determining the actual locations of edge signals by peak detection and correlation, and adjusting for variations in the number of points in the test and reference data sets.

20 Claims, 10 Drawing Sheets fig. 1 fig. 2 fig. 3 fig. 4 fig. 5 fig. 7 fig. 8 fig. 9 fig. 10 fig. 12 fig. 13

EDDY CURRENT INSPECTION METHOD EMPLOYING A PROBE ARRAY WITH TEST AND REFERENCE DATA ACQUISITION AND SIGNAL PROCESSING

BACKGROUND OF THE INVENTION

The present invention relates generally to the inspection of components employing eddy current techniques and, more particularly, to the processing of signals from an eddy current probe array which is mechanically scanned in one direction.

Eddy current inspection is a commonly used technique for non-destructively detecting discontinuities or flaws in the surface of various components, for example aircraft engine parts. Very briefly, eddy current inspection is based on the principle of electromagnetic induction in which a drive coil is employed to induce eddy currents within the material under inspection, and secondary magnetic fields resulting from the eddy currents are detected by a sense coil, generating signals which are subsequently processed for the purpose of detecting flaws.

Eddy current testing for flaws in conductive materials is typically done by mechanically scanning a single probe in two dimensions. For example, patent application Ser. No. 07/772,761, filed Sep. 16, 1991, now U.S. Pat. No. 5,345,514, entitled "An Improved Method for Inspecting Components Having Complex Geometric Shapes" describes methods for interpreting eddy current image data acquired by a single probe, particularly in the context of inspecting a high pressure turbine (HPT) disk dovetail slot.

Eddy current images as created by scanning a surface with a single probe are usually highly over-sampled because the probe is moved in incremental steps that are just a small fraction of the dimension of the active area of the probe. Therefore, as the probe moves across a defect, numerous image data points "detect" the defect, i.e. they have amplitude values that correspond to defect levels. This over-sampling occurs in two dimensions, so an image of a point source (e.g. a small hole) actually appears as the active area of the probe, rather than just the point it represents. Because of this, image processing routines that take advantage of the highly correlated image information can be used to improve the likelihood of detecting small defects in eddy current images. The above-identified application Ser. No. 07/772,761 discloses one such approach to image processing.

Although effective, the single probe scanning method is time consuming. Probe arrays have been developed to improve the scanning rate, as well as to increase flaw detection sensitivity. Probe arrays include several identical elements that are scanned simultaneously in parallel. Eddy current arrays and array systems have been described in the literature, for example Bert A. Auld, "Probe-Flaw Interactions with Eddy Current Array Probes", Review of Progress in Quantitative NDE 10, edited by D. O. Thompson and D. E. Chimenti (Plenum Press, New York, 1991), pages 951–955; A. J. Bahr, "Electromagnetic Sensor Arrays—Experimental Studies", Review of Progress in Quantitative NDE 10, edited by D. O. Thompson and D. E. Chimenti (Plenum Press, New York, 1991) pages 691–698; Yehuda D. Krampfner and Duane D. Johnson, "Flexible Substrate Eddy Current Coil Arrays", Review of Progress in Quantitative NDE 7, edited by D. O. Thompson and D. E. Chimenti (Plenum Press, New York, 1988), pages 471–478; and Mirek Macecek, "Advanced Eddy Current Array Defect Imaging", Review of Progress in Quantitative NDE 10, edited by D. O. Thompson and D. E. Chimenti (Plenum Press, New York, 1991), pages 995–1002.

As another example, General Electric High Density Interconnected (HDI) technology has been used to fabricate flexible eddy current probe arrays. In particular, Hedengren et al. application Ser. No. 07/696,455, filed May 6, 1991, the entire disclosure of which is hereby expressly incorporated by reference, discloses an eddy current probe array comprising a plurality of spatially correlated eddy current probe elements disposed within a flexible interconnecting structure which may be employed to collect a discrete plurality of spatially correlated eddy current measurements for non-destructive near surface flaw detection. An array of such elements can, in a single unidirectional scan, accommodate inspecting an area covered by the active width of the array. This array structure can flexibly conform to accommodate inspection of large, irregular, curved conductive surfaces which cannot readily be inspected by conventional means.

Although eddy current probe arrays have a speed advantage, in contrast with single probe scanning there is no over-sampling along the common axis of the elements; only a single measurements can be acquired across the width of one element, and a small defect may be detected only by one element. Therefore, image processing as applied to images created by single probe scanning cannot be used as effectively for array data. Instead, signal processing may be applied to individual data traces acquired for each element in a direction perpendicular to a row of elements.

Eddy current data from parts with irregular geometries is particularly difficult to process and analyze. One challenging problem arises from the fact that the probe moves from air past a first edge of a part being inspected, over the surface of the part and then over a second edge of the part back into air. This gives rise to potentially large signals at the edges. Any signals due to cracks at the edges must be detected even though they are buried in the large edge signals.

Although there are known methods for emphasizing flaw signals, such as the background subtraction method, difficulties arise when applied to interpreting data from eddy current probe arrays. For example, alignment between test waveforms and reference waveforms is critical, and yet a mechanical scanner is unable to return to an identical initial position to originate data collection time after time. Moreover, various factors such as "lift off" introduce DC level variations.

SUMMARY OF THE INVENTION

Accordingly, it is an object of the invention to provide a method for processing and interpreting data acquired from an eddy current probe array inspection system which increases the probability of detecting defects.

It is a related object of the invention to provide such a method of processing and interpreting data which enables the detection of signals due to cracks at edges of a part under inspection to be detected, even though the signals due to cracks are buried in large edge signals.

It is yet another object of the invention to provide a method for the interpretation of eddy current array inspection data which can be automated and easily integrated into a production environment.

Briefly, and in accordance with an overall aspect of the invention, it is recognized that, for a specific geometry, the edge signals are repeatable and can be reduced by combining them with the edge signals from one or more different but similar reference parts, by suitably applying a known background subtraction method described, for example, in "Digital Image Processing" by Gonzalez and Wintz, 1987.

More particularly, the invention provides an eddy current method for inspecting a component including at least one structural portion having at least one edge and, in many cases first and second accessible edges. Test and background reference data are acquired by employing an eddy current probe array to scan the structural portion. The scan covers at least an edge and the structural portion and, typically, the scan is from a scan starting position outside the first edge to a scan ending position outside the second edge. The eddy current probe array has a plurality of array elements arranged such that the array elements follow different parallel tracks to produce, during a scan, a corresponding plurality of test waveform signals. For example, the array elements may be arranged in one or several rows. In the case of a two-row array, the rows are staggered to in effect interlace the tracks, for a closer spacing between tracks, and are spaced in a direction along the parallel tracks. The rows may extend either in a direction perpendicular to the parallel tracks, or the row or rows may be diagonal. The test waveform signals are sampled in a conventional manner to acquire a test data set corresponding to each of the test waveform signals.

The eddy current probe array is employed to likewise scan a reference structural portion to produce a corresponding plurality of background reference data signals, which are also sampled to acquire a background reference data set corresponding to each of the background reference data signals.

Preferably, after the data are acquired, the data sets are normalized, such as by removing DC levels and trends.

Then, for each test data set and its corresponding background reference data set, the two data sets are aligned. In the case of a scan covering just one edge and the structural portion, the data sets are aligned such that data set portions representing signals produced when scanning over the edge coincide. In the case of a scan covering first and second edges, the two data sets are aligned such that data set portions representing signals produced when scanning over the first edge coincide, and data set portions representing signals produced when scanning over the second edge coincide. This alignment includes, for each background reference data set, finding peaks representing signals produced when scanning over the edge or edges, and then extracting a correlation kernel for the peak or for each of the peaks based on a range of data points on either side of the peak. Any suitable technique may be employed for finding peaks, such as finding the positions of local minima and maxima within predetermined regions of the data sets, or employing a derivative-based approach. The kernels thus extracted from the background reference data sets are then employed to determine the corresponding positions in each of the test data sets representing signals produced when scanning over the edge or over the first and second edges, employing a correlation technique. Where first and second edges are scanned, and if necessary, the background reference data sets are resized by adding or removing data points in a uniform region of the background reference data sets as required.

Finally, for each test data set and corresponding background reference data set, the two data sets are combined, such as by subtraction, to produce a corresponding combined data set emphasizing flaw signals represented by differences in the two data sets.

Thereafter, the combined data sets may be enhanced by employing a priori information about specific characteristics of a flaw signal. Then, candidate defect signals are identified, a defect measure is calculated for each defect signal, and candidate defect signals are classified as a defect if the defect measure is not within acceptable limits.

BRIEF DESCRIPTION OF THE DRAWINGS

While the novel features of the invention are set forth with particularity in the appended claims, the invention, both as to organization and content, will be better understood and appreciated, from the following detailed description taken in conjunction with the drawings in which:

DETAILED DESCRIPTION

Figure 1:
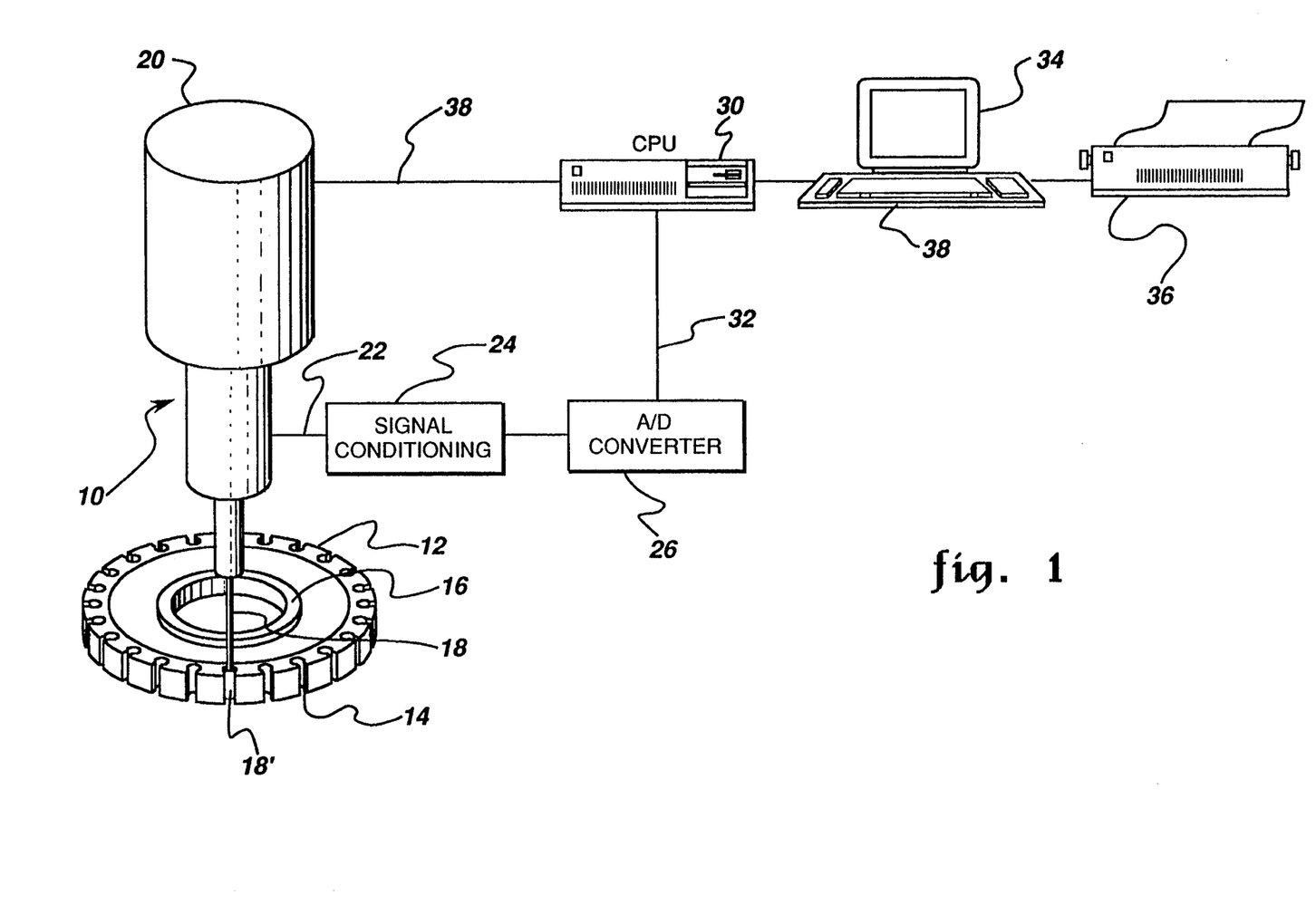
FIG. 1 is an overview of an eddy current inspection system employing the present invention.

Referring initially to FIG. 1, an automatic eddy current surface flaw detection apparatus 10 is depicted inspecting a workpiece 12, in the representative form of a high pressure turbine (HPT) disk having dovetail slots 14. The dovetail slots 14 thus comprise structural portions to be inspected. It will be appreciated that this particular application is representative only, as the invention may be employed in the inspection of any workpiece having a complex geometry which may repeat or include a plurality of similarly shaped portions, such as the teeth of a gear.

The turbine disk 12 is mounted on a fixture 16 of the apparatus 10 to hold the disk 12 in place during inspection. The apparatus 10 includes an eddy current array probe 18 on which a probe array 18' is mounted. A suitable probe array 18' is disclosed in the above-incorporated application Ser. No. 07/696,455 and includes a plurality of array elements in the form of sense coils. Preferably, each array element comprises two coils differentially connected and operating in a reflection mode with a drive coil integrated within the array structure. However, such is exemplary only, and the present invention is not limited to any particular form of array element.

The eddy current array probe 18 is mounted to a probe manipulator 20 which moves the array probe 18 vertically within the dovetail slot 14 to scan the interior of the slot 14 for inspection. The manipulator 20 is preferably a six-axis manipulator, such as a Unidex, manufactured by Aerotech Inc., or the like. The array probe 18 is electrically connected through a data link 22 to suitable signal conditioning circuitry 24. Output signals from the signal conditioning circuitry 24 are sampled by a multi-channel A/D convertor 26, which are then applied to a suitable processor 30 for storage and further analysis. Signal traces or two-dimensional digital images may be displayed on a video monitor 34, or on a printer 36. A keyboard 38 is provided to facilitate operator control of the inspection process. Movement of the probe manipulator 20 is also controlled by the CPU 30 as represented by line 38.

Figure 2:
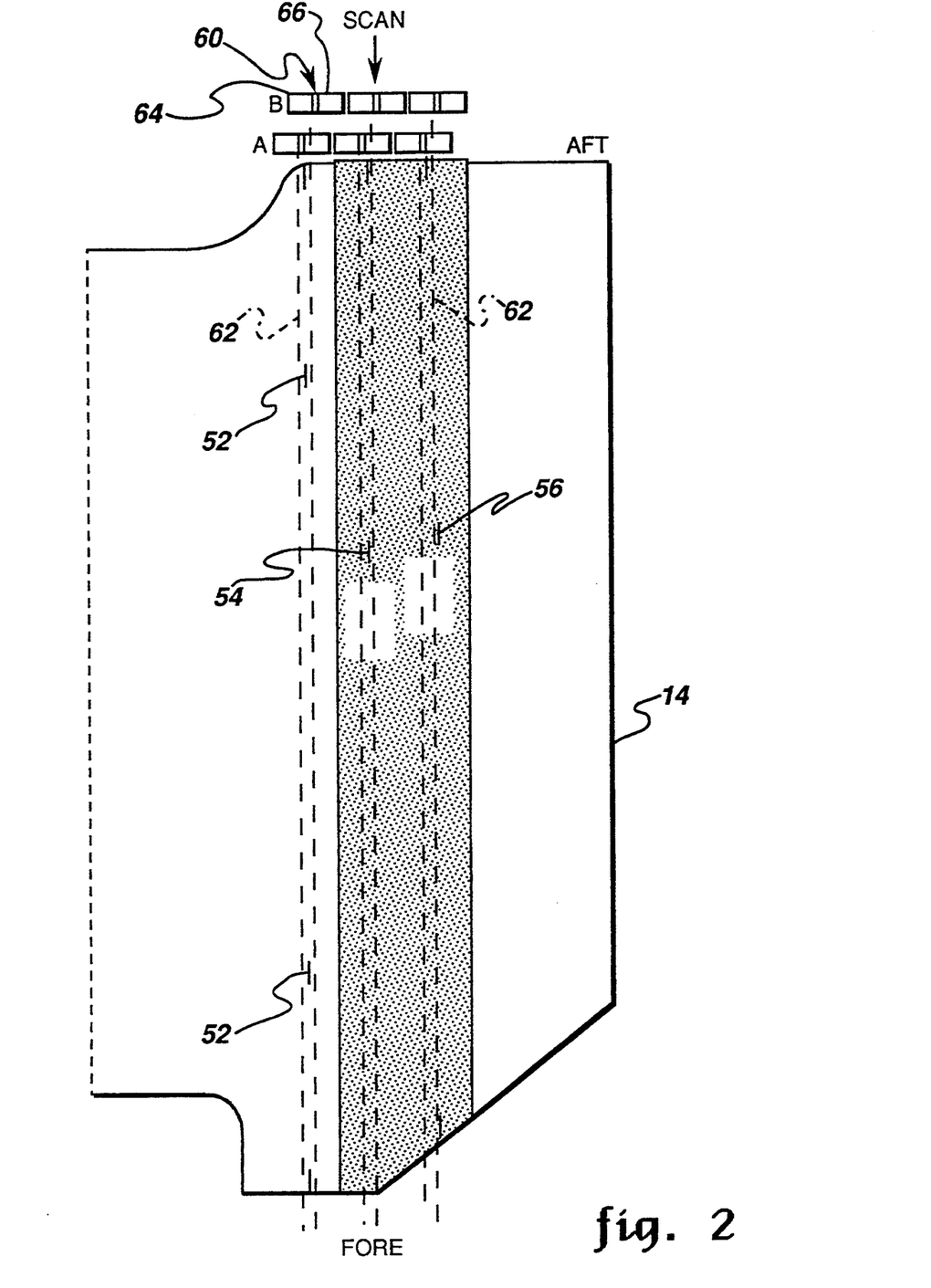
FIG. 2 is a representative drawing of a "flattened" version of one-half of a high pressure turbine disk dovetail slot being examined, showing a two-row array of probe elements in a position near the beginning of a scan.

FIG. 2 in general is an enlarged view of a single slot 14 of the FIG. 1 workpiece 12, with the probe array 18' in a position near the beginning of a scan. FIG. 2 is a "flattened" version of one-half of the outer portion of a slot 14. In other words, FIG. 2 represents what the slot surface would resemble if its curved portions were physically straightened; thus, FIG. 2 is not a sectional view.

Three groups 52, 54 and 56 of vertically aligned electro-discharge machining (EDM) notches are present in the slot 14. The first group features two 0.017" L×0.017" D edge notches, a 0.034" L×0.017"D body notch and a 0.012" L×0.006" D body notch. The second group contains a 0.006" L×0.006" D edge notch and a 0.100" L×0.010" D body notch. The third group contains two 0.017" L×0.017" D edge notches and a 0.034" L×0.017" D body notch. The inspection specification for this area requires detection of the 0.034" L×0.017" D body notches and 0.017" L×0.017" D edge notches.

In FIG. 2, the probe array 18' included in the array probe 18 more particularly may be seen to comprise a plurality of array elements in the form of sensor elements 60 arranged in two staggered rows "A" and "B", each row "A" and "B" extending in a direction perpendicular to parallel tracks 62 which the sensor elements 60 follow during a scan. Each of the sensor elements 60 comprises a pair of coils 64 and 66 which are electrically differentially connected, preferably for use with an integrated drive coil and operating in a reflection mode.

Although the array elements are shown in two staggered rows to in effect interlace the tracks for a closer spacing between tracks, it will be appreciated that other arrangements may be employed, such as arranging the array elements along one or more diagonal rows relative to the direction of scanning.

Figure 3:
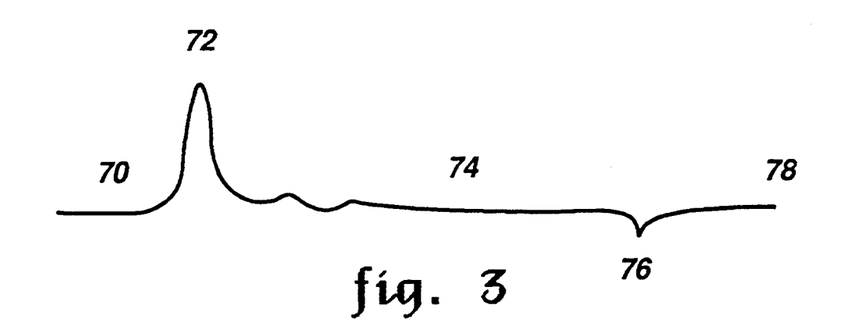
FIG. 3 is a typical dovetail slot data trace without significant flaws.

FIG. 3 represents a typical dovetail data trace, such as is produced by a single one of the array elements 60 during a scan of the dovetail slot 14.

More particularly, in a dovetail scan the probe 18 starts in air, enters and moves through the dovetail slot 14, and finally exits the slot 14 and ends in air. A segment of a dovetail slot 14 often has one angled edge surface and one fairly flat edge surface. For a differential probe element, this results in a data trace similar to the one shown in FIG. 3.

Region 70 in FIG. 3 corresponds to the response of the probe element in air before it reaches the slot 14. The large peak at 72 corresponds to the probe element crossing an angled surface into the slot 14. Region 74 is the response of the probe element to the slot itself. Region 76 is the signal peak produced as the probe leaves the slot 14 by a fairly flat surface, and region 78 is once again an air signal.

Figure 4:
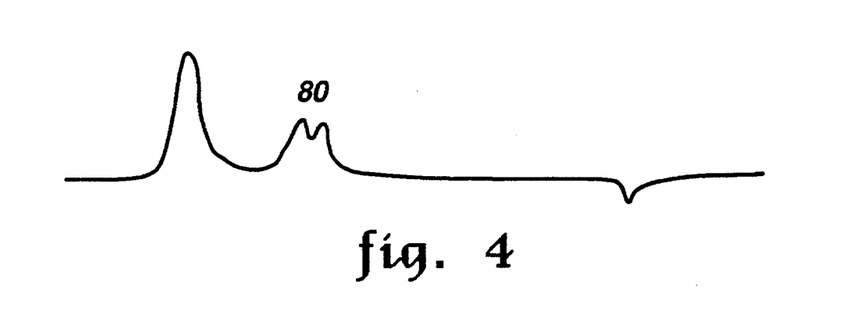
FIG. 4 is a dovetail slot test data trace including a signal due to a notch.

FIG. 4 represents a similar data trace, but with a double peak at 80 which is due to an EDM notch. For convenience, FIG. 3 is considered to be a reference trace, while FIG. 4 is considered to be a test trace.

Inspection of dovetail slots is an exemplary application only, and there are other inspection situations where only a single edge and a portion of a structural component are scanned. Reasons for such inspection situations include obstructions which prevent a complete scan from a scan starting position outside a first edge to a scan ending position outside a second edge, and structural components of large size. In such situations it is sufficient for the scan to cover just one edge, assuming the scan rate is constant, such that just one of the FIG. 3 peaks 72 and 76 is present. Either peak 72 or 76 alone may be employed for registration purposes, as is described hereinbelow in detail.

There are several approaches to providing a reference structural portion to provide the background reference data signals. A simple and effective approach is to use traces from a single data set from a clean slot 14 known to be free of defects, which may be scanned immediately prior to or after acquiring test data, or may be stored in a memory for future use.

To successfully combine the test (FIG. 4) and reference (FIG. 3) traces, they must be registered to the same position, have similar DC offsets and dynamic range, be essentially flat where there is no defect or edge signal, and have the same number of sample points through the slots. The present invention provides a method of processing the test and reference traces so that a characteristic background signal can be successfully subtracted from the test signal.

Figure 5:
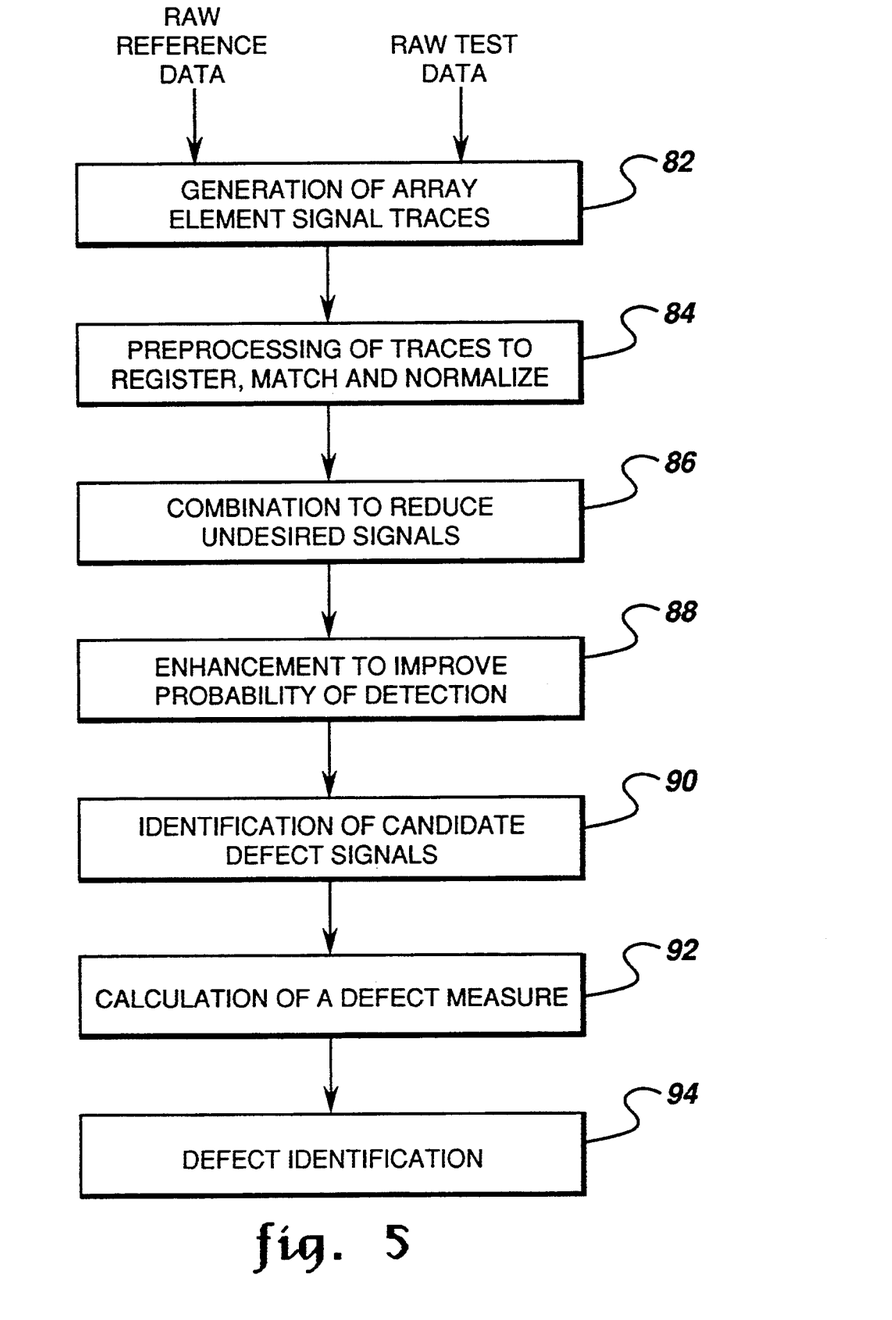
FIG. 5 is a flow chart depicting array signal processing in accordance with the invention in overview.

FIG. 5 is an overall flowchart of a signal processing technique in accordance with the invention, which employs a pre-processing/registration algorithm in an implementation of the background or reference subtraction technique.

In overview, and based on the signal waveform as shown in FIGS. 3 and 4, edge signals from each of the traces are employed to register the test data with the reference data. There are, however, a number of complications. First, where scanning is over first and second edges, the spacing between the two edge signals must be identical for the background subtraction method to work. A difference in spacing of several data points between the edge signals is possible since dovetail parts are often hand finished around the edges. Secondly, it is impossible for the mechanical scanner to return to the identical position to originate data collection time after time. This can cause a few data points of variation in the distance between the edge signal or signals and the start of the data set. Accordingly, the registration process is based on the signals themselves, rather than on a mechanical reference provided by the manipulator.

In overview, Box 82 of FIG. 5 represents the generation of array element signal traces, including data acquisition, of reference data and test data. Box 84 represents pre-processing of traces to register, match and normalize, thus simplifying subsequent procedures. Registering and matching involve locating edge signals in the reference trace and corresponding points in the test trace, and modification of traces to ensure proper registration.

Box 86 depicts the step of combination by reference subtraction to reduce undesired (edge) signals, while emphasizing flaw signals. Box 88 represents enhancement to improve probability of detection. Enhancement schemes take advantage of a priori information about specific characteristic features of the defect signals, and may be employed individually for each trace, or adjacent traces may be combined by a function before enhancement is done. Candidate defect signals are identified in Box 90, a defect measure is calculated in Box 92, and defects are identified in Box 94. The final result is a trace which identifies the positions of possible defects.

Figure 6:
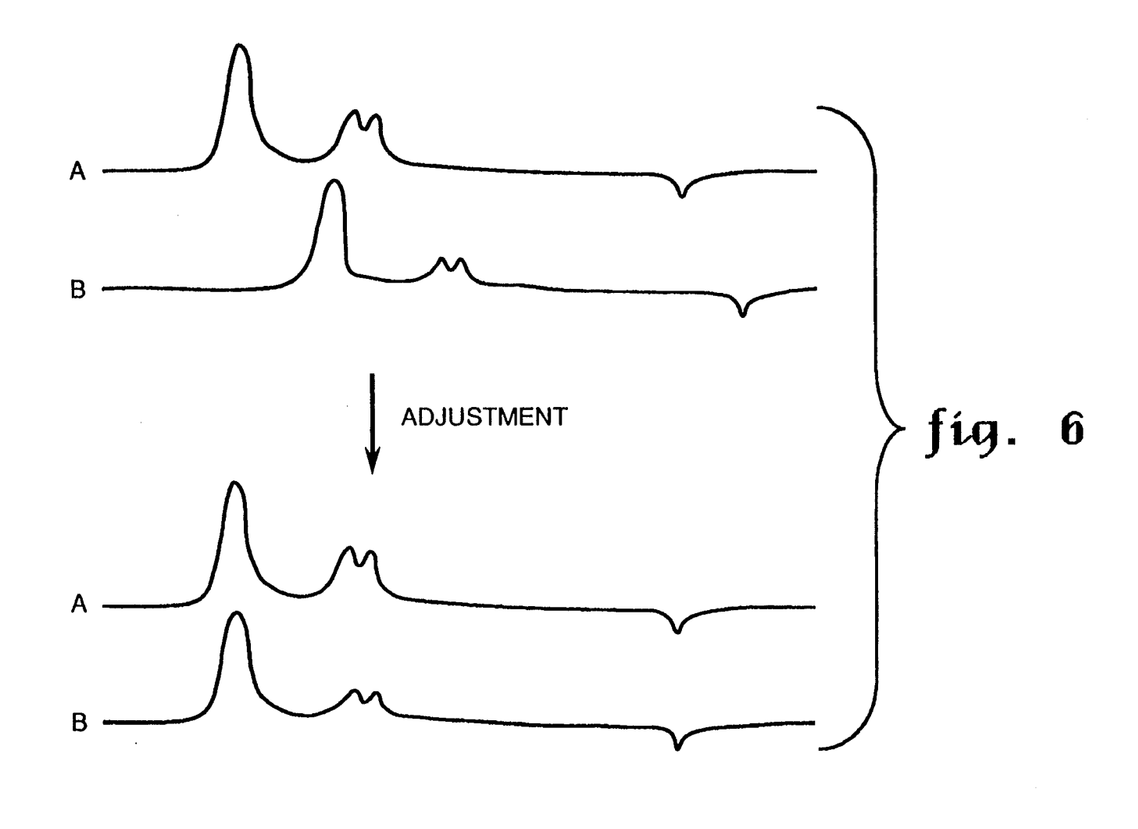
FIG. 6 shows representative signal traces from two elements in different rows of the array during a scan, illustrating the effect of the spatial offset between the two rows, and the result of adjustment by shifting the data sets to adjust for spatial offset.

As noted hereinabove with reference to FIG. 2, to ensure surface coverage, the probe array 18' is designed employing two staggered rows "A" and "B", resulting in a form of interlaced scan. As the array 18' is scanned, the first row "A" detects the edges and flaws of the slot before the second row "B", resulting in what may be viewed as a spatial offset. To compensate for this, the data sets are shifted relative one to the other as required to compensate for the variations in relative position. This operation is depicted in FIG. 6, wherein the upper pair of traces represent the data prior to shifting, and the lower pair of traces depict the result after shifting. The geometric design of the coils and the sampling rate determine the number of data points to shift the traces. It will be appreciated that the required shift is constant for a given probe array and a specific sampling rate.

Figure 7:
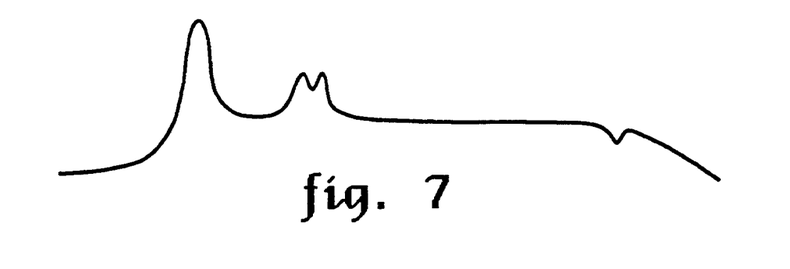
FIG. 7 depicts a representative waveform prior to processing to remove DC levels and trends.

As shown in FIG. 7, individual traces may exhibit a trend, which would prevent successful signal combination for later thresholding. Such traces may be "flattened" into the shape as shown in FIG. 9, employing, for example, the algorithm of FIG. 8. In brief summary, with reference to FIG. 8, the trace is median-filtered in multiple stages to remove the notch and edge signals, after which the filtered trace is subtracted from the original trace to yield the flat trace of FIG. 9.

Figure 8:
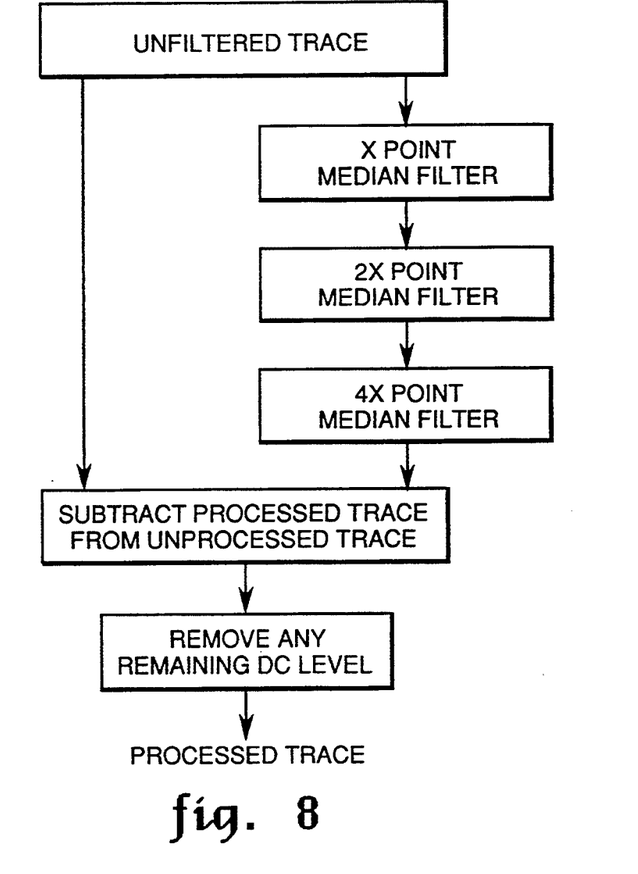
FIG. 8 is a flow chart of an algorithm for pre-processing to remove DC and low frequency components.
Figure 9:
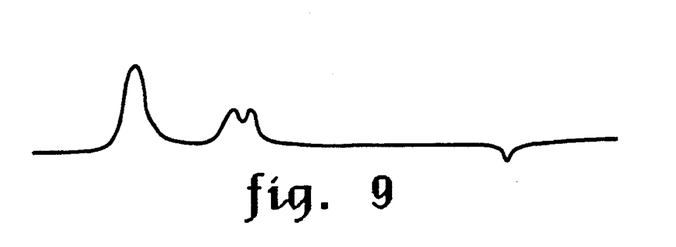
FIG. 9 shows the waveform of FIG. 6 after pre-processing by the algorithm of FIG. 8.

In FIG. 8, the value x which goes into a bank of median filters is dependent on the sizes of the flaws which must be found and the sampling rate. It is critical that the value 4x be at least twice as large as the width of the maximum flaw size in data points. (It is also important to note that the values x, 2x and 4x are only approximate since a median filter is most conveniently used when x, 2x and 4x are all odd). So long as x is chosen properly, the bank of filters represented in FIG. 8 produces a result which removes the low frequency trends, preserves any flaw signals, and produces no artifacts.

After the reference and test traces have been normalized, the peaks due to the entry and exit from the slot are identified and lined up for the test and reference traces. Finding the peaks in the reference traces is not particularly difficult. However, in the case of the test traces, large flaw signals may be present, which can render useless a simple peak detection strategy.

Figure 10:
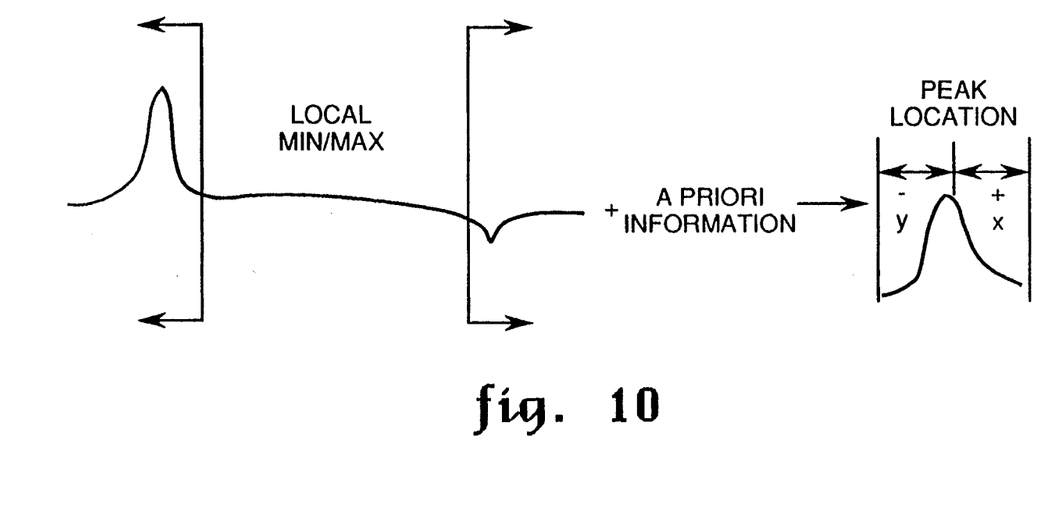
FIG. 10 depicts the step of kernel extraction from a reference trace.

In accordance with the invention, peaks are located in the reference traces, and a kernel extracted for the peaks, to be subsequently employed in a correlation process. FIG. 10 illustrates the process of finding the peaks in the reference trace. A simple way is to locate the minimum and maximum data point values in regions of the data where edge signals are expected to occur. The polarity of an edge signal from a given array element is constant from slot to slot. Thus, the minimum and the maximum locations can be combined with a priority knowledge about the expected polarity to determine the location of the peak in the edge signal. A portion of +x and −y data points is extracted from the reference trace around the peak location, comprising the kernel.

The correlation kernel is thus a portion of the edge signal from the reference trace. The kernel width providing the best results is located on the portion of the edge signal which was between the peak and the air region. In cases where a scan covers two edges, two kernels are extracted from each reference trace, one for each edge signal.

While peak detection works well for locating the edge signals in reference traces, it does not do as good a job in test traces. An edge crack distorts an edge signal, which can cause a regional minimum/maximum operation to choose as the test peak a position on the test trace which does not correspond to the position found for the reference trace.

Figure 11:
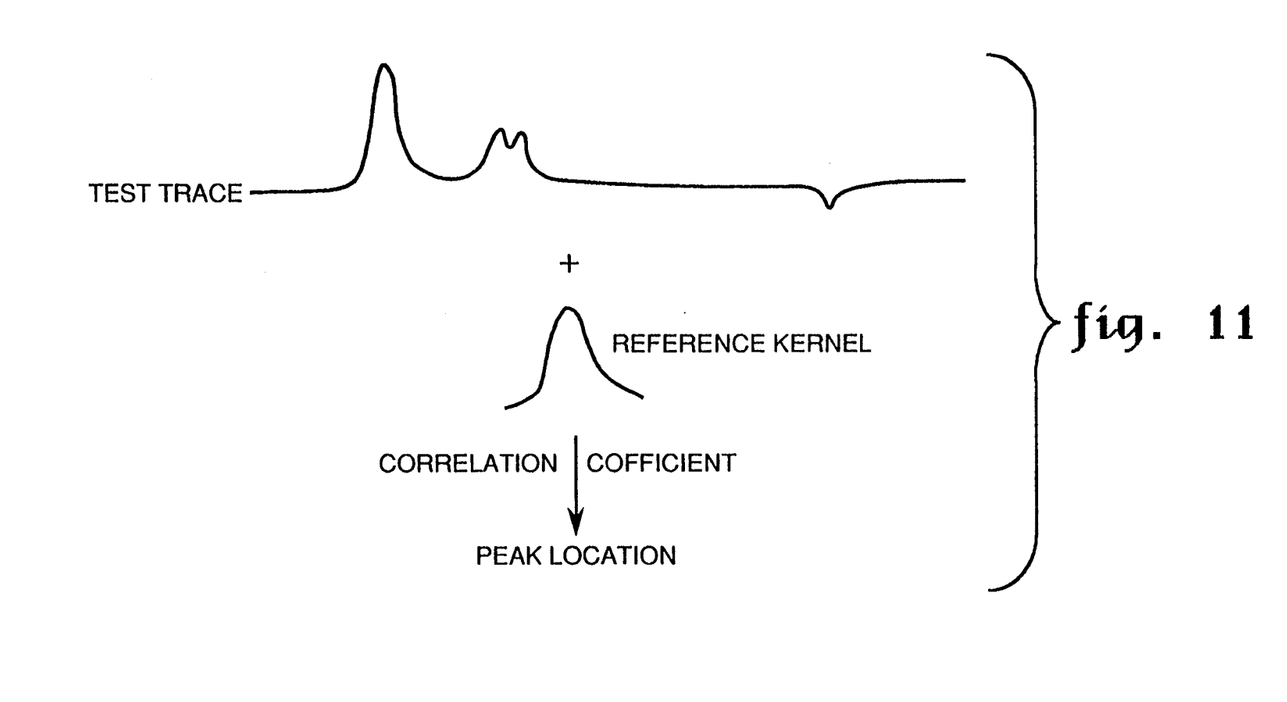
FIG. 11 depicts the step of employing the reference kernel to locate the position of a peak in a test waveform.

Thus, and as depicted in FIG. 11, a correlation coefficient technique is used to accurately determine the corresponding position of edge signals in the test traces. A suitable correlation coefficient technique is described, for example, in Digital Imaging Processing, by Gonzalez and Wintz, 1987, page 426. With this technique, correlation coefficients are computed using the kernel from the reference trace and a region around the edge signal in the test trace, the location with the maximum correlation coefficient in this region is judged to be the corresponding position of the edge signal in the test trace. As another consideration, the number of points between the entry to and the exit from the slots can vary for the test and reference data sets, for example, due to hand finishing of the part. If such is the case, subtraction of the reference trace from the test trace would not result in cancellation of the edge signals as intended; in fact, the edge signals may be undesirably enhanced.

Figure 12:
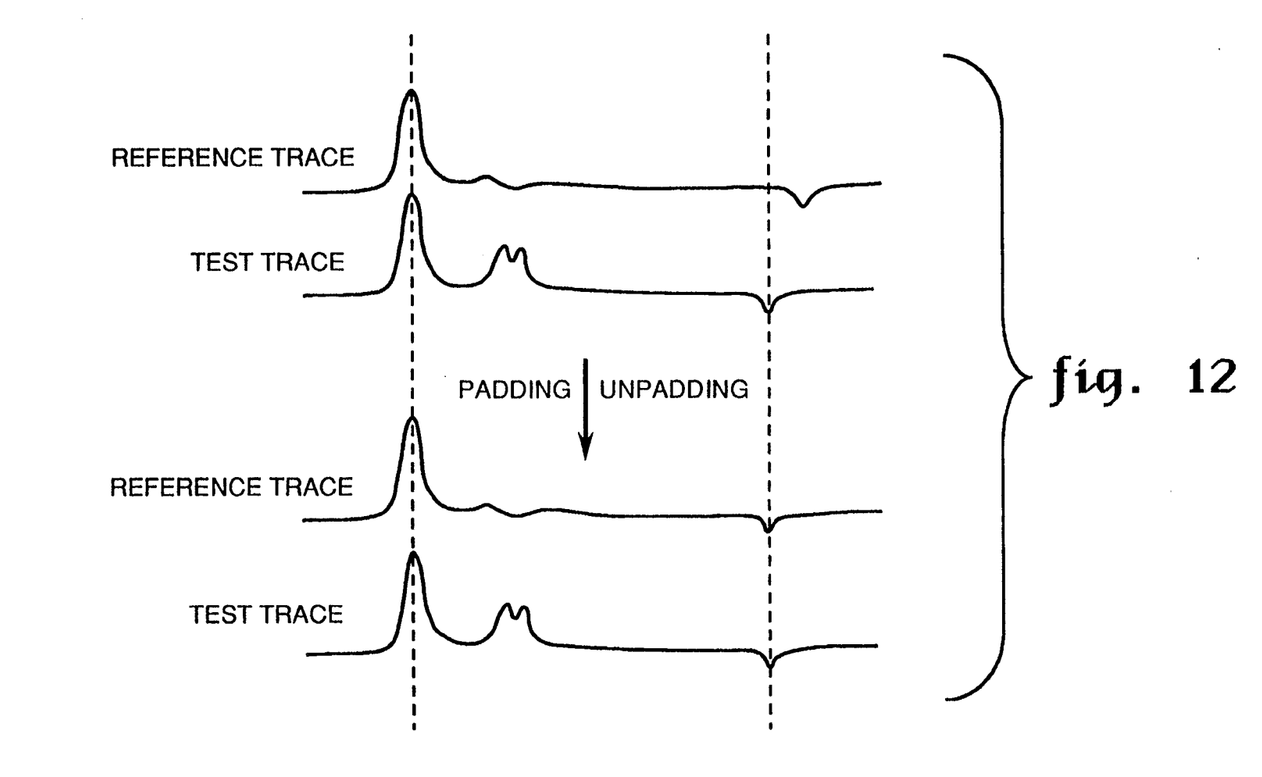
FIG. 12 depicts resizing a reference trace.

Thus, and as depicted in FIG. 12, to compensate for this potential problem, the spacing between the peaks of the reference trace is made the same by increasing or reducing the number of points, as required, until they agree with the number of points between the peaks of the test trace. This is done in a region of the reference trace which is relatively uniform that is, without significant amplitude variations, so that the insertion or deletion of data points does not cause any particular distortion.

Figure 13:
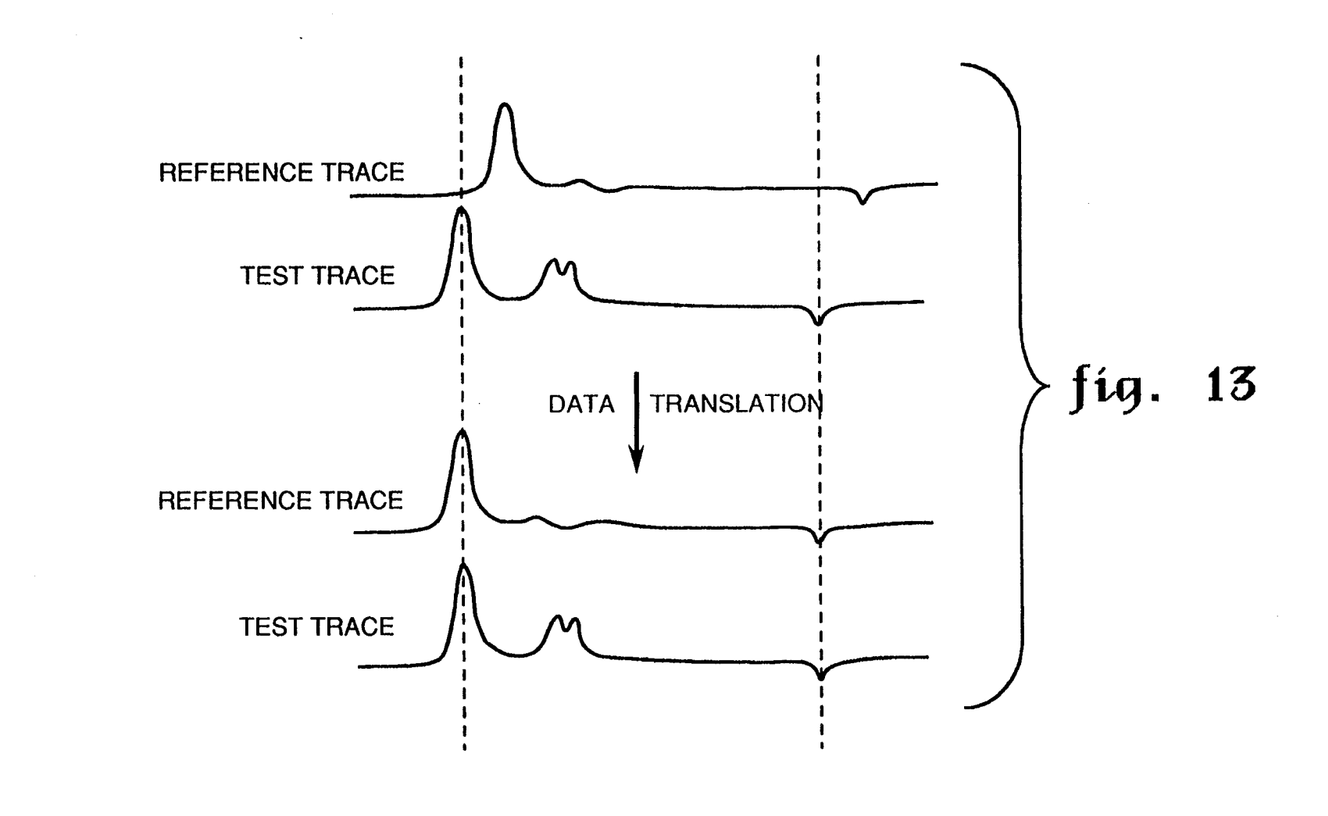
FIG. 13 depicts the step of aligning a representative reference trace and test trace.

FIG. 13 depicts the step of aligning the traces. A difference in the position of the edge traces with respect to the start of the data traces is possible, for example due to mechanical manipulator limitations. Such variation, if present, is corrected using information about the edge signal locations acquired earlier. Since the traces now have the same length, aligning the entry edge signals also aligns the exit edge signals. Thus, the locations of the entry edge signals can be used to translate the traces and align the edge signals as illustrated in FIG. 13. After the traces have been properly aligned, they can be subtracted. A straight subtraction of the processed test trace from the processed reference trace, or vice versa, is all that is required to produce a combined data set emphasizing the flaw signals represented by the differences in the two data sets.

The signal represented by the combined data set may be thresholded directly to detect defect candidates, or it may be enhanced before thresholding. Enhancement that takes advantage of a priori information about specific characteristic features of a defect signal may be used individually for each trace, or adjacent traces may be combined by a function before the enhancement is done. The final result is a binary trace that identifies the positions of potential defects. A criterion for acceptability is then applied to determine the severity of each potential defect.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An eddy current method for inspecting a component including at least one structural portion having at least one edge, said method comprising:

acquiring test and background reference data by scanning the structural portion employing an eddy current probe array having a plurality of array elements arranged such that the array elements follow different parallel tracks over the edge and over the structural portion to produce during a scan a corresponding plurality of test waveform signals, and sampling the test waveform signals to acquire a test data set corresponding to each of the test waveform signals, and employing the eddy current probe array to likewise scan a reference structural portion having at least one edge corresponding to the structural portion to produce a corresponding plurality of background reference data signals, and sampling the background reference data signals to acquire a background reference data set corresponding to each of the background reference data signals;

for each test data set and its corresponding background reference data set, aligning the two data sets such that data set portions representing signals produced when scanning over an edge coincide; and for each test data set and its corresponding background reference data set, combining the two data sets to produce a corresponding combined data set emphasizing flaw signals represented by differences in the two data sets.

2. A method in accordance with claim 1, wherein said combining step comprises subtraction.

3. A method in accordance with claim 1, which further comprises, following said combining step, enhancing the combined data sets by employing information about specific characteristics of a flaw signal.

4. A method in accordance with claim 3, which further comprises, following said enhancing step, identifying candidate defect signals, calculating a defect measure for each defect signal, and classifying as a defect if the defect measure is not within acceptable limits.

5. A method in accordance with claim 1, which further comprises, following said step of acquiring data, shifting the data sets relative to one another as required to compensate for any variations in relative positions of array elements in a direction along the parallel tracks.

6. A method in accordance with claim 5, wherein:

said step of acquiring data comprises employing an eddy current probe array having a plurality of array elements arranged in at least two staggered rows spaced in a direction along the parallel tracks, and the rows spaced in a direction along the parallel tracks; and wherein said step of shifting the data sets compensates for the spacing between array element rows.

7. A method in accordance with claim 6, wherein said step of acquiring data comprises employing an eddy current probe array having a plurality of array elements arranged in at least two staggered rows each extending in a direction perpendicular to the parallel tracks.

8. A method in accordance with claim 1, which further comprises, following said step of acquiring data, normalizing said data sets.

9. A method in accordance with claim 8, wherein said step of normalizing comprises removing DC levels.

10. A method in accordance with claim 8, wherein said step of normalizing comprises removing trends.

11. A method in accordance with claim 8, wherein said step of normalizing comprises removing DC levels and trends.

12. A method in accordance with claim 1, wherein said step of aligning comprises:

for each background reference data set, finding a peak representing signals produced when scanning over the edge, and extracting a correlation kernel for the peak based on a range of data points on either side of the peak; and for each test data set, determining the corresponding positions of a data region representing signals produced when scanning over the edge by correlation with the correlation kernels.

13. A method in accordance with claim 12, wherein said step of finding a peak comprises finding the position of a local minimum and maximum within a predetermined region of each of the background reference data sets.

14. A method in accordance with claim 12, wherein said step of finding peaks is derivative-based.

15. An eddy current method for inspecting a component including at least one structural portion having first and second edges, said method comprising:

acquiring test and background reference data by employing an eddy current probe array to scan the structural portion from a scan starting position outside the first edge to a scan ending position outside the second edge, the eddy current probe array having a plurality of array elements arranged such that the array elements follow different parallel tracks, to produce during a scan a corresponding plurality of test waveform signals, and sampling the test waveform signals to acquire a test data set corresponding to each of the test waveform signals, and employing the eddy current probe array to likewise scan a reference structural portion having first and second edges corresponding to the structural portion to produce a corresponding plurality of background reference data signals, and sampling the background reference data signals to acquire a background reference data set corresponding to each of the background reference data signals;

for each test data set and its corresponding background reference data set, aligning the two data sets such that data set portions representing signals produced when scanning over the first edge coincide, and data set portions representing signals produced when scanning over the second edge coincide; and for each test data set and its corresponding background reference data set, combining the two data sets to produce a corresponding combined data set emphasizing flaw signals represented by differences in the two data sets.

16. A method in accordance with claim 15, wherein said step of aligning comprises:

for each background reference data set, finding peaks representing signals produced when scanning over the first and second edges, and extracting a correlation kernel for each of the peaks based on a range of data points on either side of the peak; and for each test data set, determining the corresponding positions of data regions representing signals produced when scanning over the first and second edges by correlation with the correlation kernels.

17. A method in accordance with claim 16, wherein said step of finding peaks comprises finding the positions of local minima and maxima within predetermined regions of the data sets.

18. A method in accordance with claim 16, wherein said step of finding peaks is derivative-based.

19. A method in accordance with claim 16, wherein said step of aligning further comprises resizing the background reference data sets as necessary by adding or removing data points in a uniform region of the background reference data sets.

20. A method in accordance with claim 15, wherein said step of aligning comprises resizing the background reference data sets as necessary by adding or removing data points in a uniform region of the background reference data sets.

* * * * *